(12) United States Patent
Hsueh et al.

(10) Patent No.: US 7,683,219 B1
(45) Date of Patent: Mar. 23, 2010

(54) HYDROFORMYLATION PROCESS

(75) Inventors: Mao-Lin Hsueh, Pingtung County (TW); Hao-Hsun Yang, Tainan (TW); Kuo-Chen Shih, Kaohsiung (TW); Tsai-Tien Su, Hsinchu (TW)

(73) Assignee: Industrial Technology Research Institute, Hsinchu County (TW)

( * ) Notice: Subject to any disclaimer, the term of this patent is extended or adjusted under 35 U.S.C. 154(b) by 0 days.

(21) Appl. No.: 12/408,722

(22) Filed: Mar. 23, 2009

(30) Foreign Application Priority Data

Sep. 16, 2008 (TW) .............................. 97135460 A

(51) Int. Cl.
*C07C 45/50* (2006.01)
(52) U.S. Cl. ...................................... 568/444; 568/445
(58) Field of Classification Search ................ 568/444, 568/445
See application file for complete search history.

(56) References Cited

U.S. PATENT DOCUMENTS 3,499,933 A * 3/1970 Pruett et al. ................. 568/444
6,365,782 B1   4/2002 Nakamura et al.

FOREIGN PATENT DOCUMENTS

WO         93/02024 A2    2/1993

* cited by examiner

*Primary Examiner*—Sikarl A Witherspoon
(74) *Attorney, Agent, or Firm*—Pai Patent & Trademark Law Firm; Chao-Chang David Pai

(57) ABSTRACT

The disclosed is about a hydroformylation of a cyclic olefin with rhodium catalyst, and specifically about the recovering of the rhodium catalyst. Aldehyde and the cyclic olefin are added into a rhodium catalyst solution to process a hydroformylation, thereby forming the product cycloalkyl aldehyde. Afterwards, the result is divided into two layers. The upper layer is substantially rhodium catalyst solution, and the lower layer is substantially cycloalkyl aldehyde and the aldehyde. After separation, the upper layer is reserved to process next hydroformylation reaction with newly added cyclic olefin.

9 Claims, No Drawings

HYDROFORMYLATION PROCESS

CROSS REFERENCE TO RELATED APPLICATIONS

This Application claims priority of Taiwan Patent Application No. 097135460, filed on Sep. 16, 2008, the entirety of which is incorporated by reference herein.

BACKGROUND OF THE INVENTION

1. Field of the Invention

The present invention relates to a hydroformylation process of cyclic olefins in the presence of a metal catalyst, and in particular relates to the separation of the desired products from the metal catalyst by phase separation.

2. Description of the Related Art

It is known in the art that compared to a heterogeneous catalyst, the homogeneous catalyst has advantages such as high reactivity, high selectivity, and a relatively milder reaction condition. However, many homogeneous catalyst systems cannot be commercially applied mainly due to difficulties in separating, recovering, and reusing the homogeneous catalysts, as it is well known.

It is known in the art that distillation is one of the favorable methods for the separation of catalysts and products. If the volatility of the product is low, the temperature required to separate the product by distillation should be higher. Most homogeneous catalysts, however, are thermal sensitive, such that the homogeneous catalyst may decompose during higher distillation temperatures and fail to be recovered for reuse. Other methods for recovering the homogeneous catalyst, e.g. chromatography, are inefficient. Accordingly, an effective and low cost separation process is critical for development of the homogeneous catalyst.

Hydroformylation of olefins with carbon monoxide (hereinafter CO) and hydrogen (hereinafter $H_2$) to form aldehydes is an important homogeneous catalytic reaction. The catalysts used for the hydroformylation of olefins are usually rhodium or cobalt catalysts, especially the rhodium catalysts due to their high reactivity and selectivity. Although rhodium catalysts have higher reactivity, their cost is much higher than the cobalt catalysts. The effective recovery and reuse of the rhodium catalysts determines their realization in the industry. If the volatility of the hydroformylation products (less than C5) is relatively high, the low temperature distillation method can be used to separate the products and the catalysts without significantly decomposing the catalysts. On the other hand, if the volatility of the hydroformylation products is high low, the abovementioned distillation method for separation is unfavorable, due to the decomposition of the catalyst at higher temperatures such that the catalyst cannot be recovered and reused, thus increasing costs.

As described above, the products from hydroformylation of cyclic olefins have a higher boiling point. If the product and catalyst are separated by vacuum distillation, a higher distillation temperature is needed, thereby decomposing the rhodium catalyst.

In WO 93/02024, a mixture of first alcohol having 1 to 3 carbon atoms and water is reported to be used as an extraction solution to separate the rhodium catalyst and high boiling-point aldehydes from hydroformylation. The efficiency of this method is, however, not good, and a better method for the efficient separation of the hydroformylation products and catalyst is still needed.

BRIEF SUMMARY OF THE INVENTION

The invention provides a hydroformylation process, comprising: (i) Reacting a cyclic olefin with carbon monoxide and hydrogen in the presence of an aldehyde and a rhodium catalyst to obtain a hydroformylation product liquid containing cycloalkyl aldehyde; (ii) the hydroformylation product liquid is then divided into a first layer and a second layer, wherein the first layer comprises substantially the rhodium catalyst and the second layer comprises substantially the aldehyde and the cycloalkyl aldehyde; and (iii) Separating the first layer from the second layer.

A detailed description is given in the following embodiments.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

The invention provides a hydroformylation process. First, a rhodium compound and an organophosphorus compound are mixed in an appropriate solvent. The rhodium compound includes rhodium trichloride hydrate ($RhCl_3 \cdot xH_2O$), dicarbonyl acetylacetone rhodium ($Rh(acac)(CO)_2$), bis(dicarbonyl chloro rhodium (($RhCl(CO)_2)_2$), carbonyl rhodium ($Rh_6(CO)_{16}$ or $Rh_4(CO)_{12}$), rhodium (III) nitrate ($Rh(NO_3)_3$, and the likes. The rhodium catalyst solution has a concentration of 10 ppm to 1000 ppm, and preferably 100 ppm to 600 ppm. The organophosphorus compound can be any phosphorus-containing organics, such as tris(2,4-di-tert-butylphenyl) phosphite, triphenylphosphite, tris(3-methyl-6-tent-butylphenyl) phosphite, tris(2,4-di-tert-butylphenyl) phosphate, di(2-tent-butylphenyl)-tert-butylphosphite, trialkyl phosphine or other suitable phosphorus-containing organics. The rhodium compound and the organophosphorus compound have a molar ratio of 1:1 to 1:300, and preferably 1:10 to 1:150. The solvent used for the catalytic reactions can be alkane, cycloalkane, or other solvent with low polarity. In one embodiment, the solvent is n-hexane.

Subsequently, cyclic olefin and aldehyde are added the rhodium catalyst solution to conduct hydroformylation. The aldehyde serves as an extraction liquid, which may dissolve the cycloalkyl aldehyde product after the hydroformylation to separate it from the rhodium catalyst solution. The aldehyde can be $C_{1-12}$ alkyl or aromatic aldehyde compound. The aldehyde and the cycloolefin cyclic olefin have a weight ratio of 1:2 to 1:20. In one embodiment, the aldehyde and the cyclic olefin has a weight ratio of 1:5 to 1:10.

The described mixture is charged in a high pressure reaction vessel to undergo a hydroformylation reaction under high pressure of $H_2$ and CO to obtain the cycloalkyl aldehyde product. The molar ratio of $H_2$ and CO in this reaction is 1:10 to 10:1, and preferably of 1:3 to 3:1. The reaction temperature is at 40° C. to 160° C., and preferably 70° C. to 140° C. The pressure of the $H_2$ and CO is between 0.5 MPa and 15 MPa, and preferably 2 MPa to 10 MPa. The cyclic olefin may have one carbon-carbon double bond or multiple carbon-carbon double bonds, such as dicyclopentadiene (hereinafter DCPD), tricyclopentadiene (hereinafter TCPD), dicyclohexadiene (hereinafter DCHD), cyclohexene, cyclohexene-1-carbaldehyde, (abbreviated CHCA), 1,2,3,6-tetrahydrobenzaldehyde, or other cyclic olefin such as methyl-3-cyclohexene-1-carboxaldehyde, methyl-4-cyclohexene-2-carboxaldehyde, 3-cyclohexene-1-carbonitrile, 3-cyclohexene-1-methanol, methyl 3-cyclohexene-1-carboxylate, 3-cyclohexene-1-carboxylate, 4-acetyl-1-cyclohexene, 1-methyl-4-cyclohexene-2-carboxylate, 1-phenyl-4-cyclohexene-2-carboxaldehyde, 1,2,3,6-tetrahydrophthalic anhydride.

The cycloalkyl aldehydes formed from cyclic olefins such as DCPD, TCPD, DCHD, cyclohexene, CHCA by hydroformylation reactions are shown in Formulae 1-8.

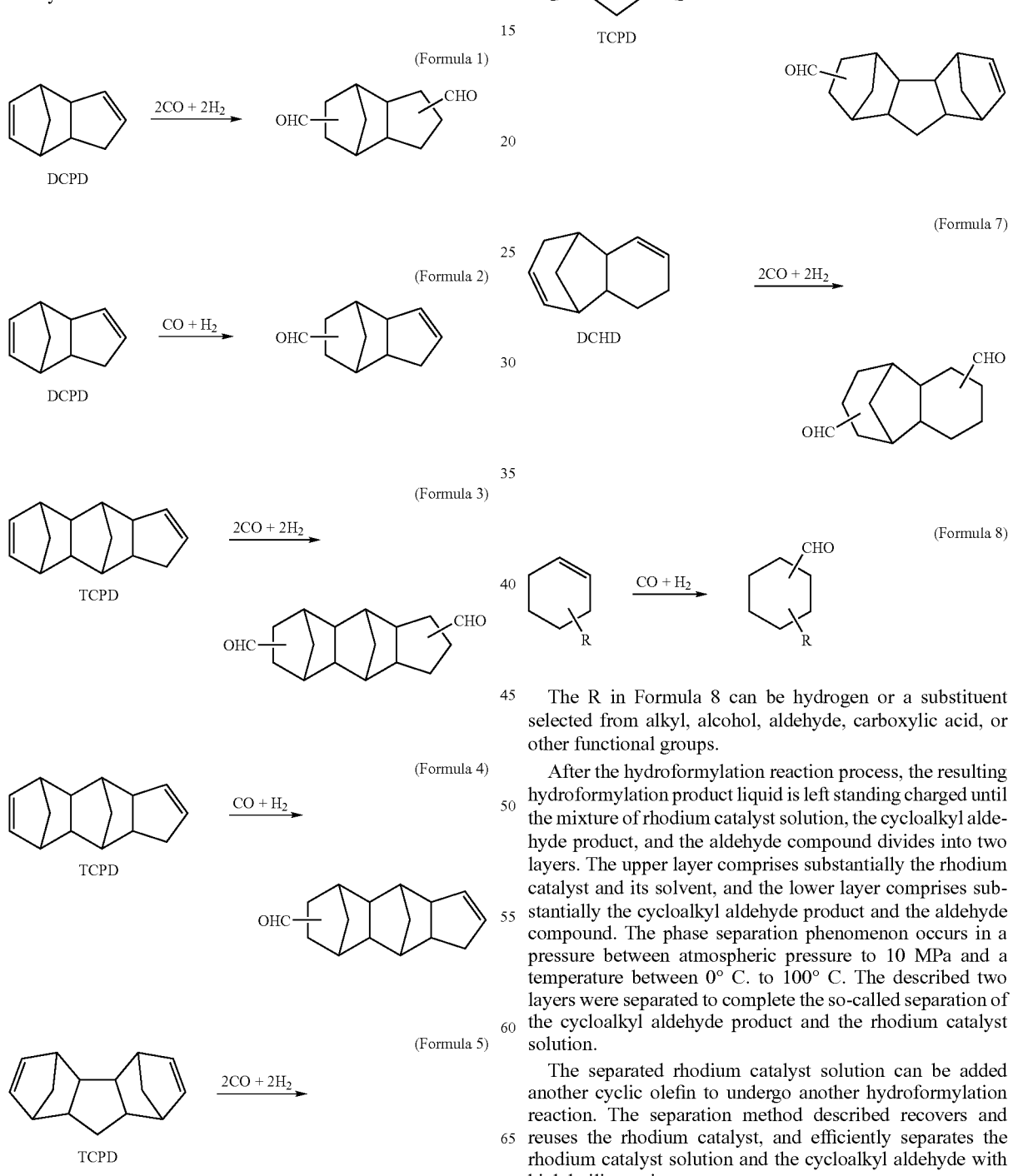

The R in Formula 8 can be hydrogen or a substituent selected from alkyl, alcohol, aldehyde, carboxylic acid, or other functional groups.

After the hydroformylation reaction process, the resulting hydroformylation product liquid is left standing charged until the mixture of rhodium catalyst solution, the cycloalkyl aldehyde product, and the aldehyde compound divides into two layers. The upper layer comprises substantially the rhodium catalyst and its solvent, and the lower layer comprises substantially the cycloalkyl aldehyde product and the aldehyde compound. The phase separation phenomenon occurs in a pressure between atmospheric pressure to 10 MPa and a temperature between 0° C. to 100° C. The described two layers were separated to complete the so-called separation of the cycloalkyl aldehyde product and the rhodium catalyst solution.

The separated rhodium catalyst solution can be added another cyclic olefin to undergo another hydroformylation reaction. The separation method described recovers and reuses the rhodium catalyst, and efficiently separates the rhodium catalyst solution and the cycloalkyl aldehyde with high boiling point.

After separation, the cycloalkyl aldehyde product and the aldehyde compound can be distillated to further separate the cycloalkyl aldehyde product and the aldehyde compound. In one embodiment, the aldehyde compound and the cycloalkyl aldehyde product have the same chemical formula, wherein the aldehyde compound comes from the product of the previous hydroformylation process. In this situation, the additional purification such as purification for separating the cycloalkyl aldehyde product and the aldehyde compound can be omitted.

The cycloalkyl alcohols can be formed from cycloalkyl aldehydes through the hydrogenation reaction are shown in Formulae 9 to 15.

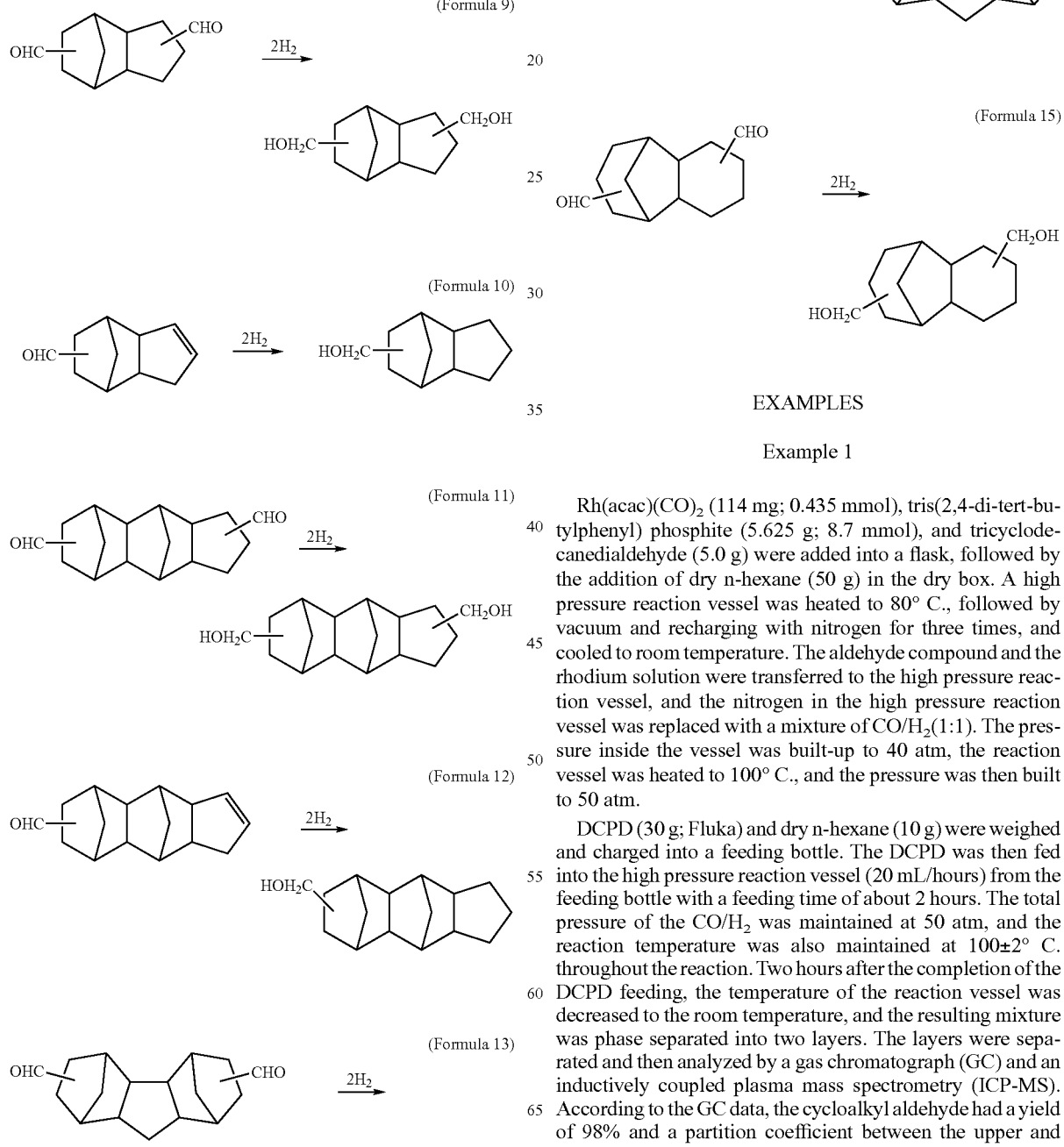

EXAMPLES

Example 1

Rh(acac)(CO)$_2$ (114 mg; 0.435 mmol), tris(2,4-di-tert-butylphenyl) phosphite (5.625 g; 8.7 mmol), and tricyclodecanedialdehyde (5.0 g) were added into a flask, followed by the addition of dry n-hexane (50 g) in the dry box. A high pressure reaction vessel was heated to 80° C., followed by vacuum and recharging with nitrogen for three times, and cooled to room temperature. The aldehyde compound and the rhodium solution were transferred to the high pressure reaction vessel, and the nitrogen in the high pressure reaction vessel was replaced with a mixture of CO/H$_2$(1:1). The pressure inside the vessel was built-up to 40 atm, the reaction vessel was heated to 100° C., and the pressure was then built to 50 atm.

DCPD (30 g; Fluka) and dry n-hexane (10 g) were weighed and charged into a feeding bottle. The DCPD was then fed into the high pressure reaction vessel (20 mL/hours) from the feeding bottle with a feeding time of about 2 hours. The total pressure of the CO/H$_2$ was maintained at 50 atm, and the reaction temperature was also maintained at 100±2° C. throughout the reaction. Two hours after the completion of the DCPD feeding, the temperature of the reaction vessel was decreased to the room temperature, and the resulting mixture was phase separated into two layers. The layers were separated and then analyzed by a gas chromatograph (GC) and an inductively coupled plasma mass spectrometry (ICP-MS). According to the GC data, the cycloalkyl aldehyde had a yield of 98% and a partition coefficient between the upper and lower layer layers of 9.6. According to the ICP-MS data, the partition coefficient of the rhodium catalyst between the upper and lower layers was 14.6.

Example 2

Rh(acac)(CO)$_2$ (107 mg; 0.407 mmol), tris(2,4-di-tert-butylphenyl) phosphite (5.625 g; 8.7 mmol), and tricyclodecanedialdehyde (4.1 g) were added into a flask, followed by the addition of dry n-hexane (50 g) in the dry box. A high pressure reaction vessel was heated to 80° C., followed by vacuum and recharging with nitrogen for three times, and cooled to room temperature. The aldehyde compound and the rhodium solution were transferred to the high pressure reaction vessel, and the nitrogen in the high pressure reaction vessel was replaced with a mixture of CO/H$_2$(1:1). The pressure inside the vessel was built-up to 40 atm, the reaction vessel was heated to 100° C., and the pressure was then built to 50 atm.

DCPD (30 g; Fluka) and dry n-hexane (10 g) were weighed and charged into a feeding bottle. The DCPD was then fed into the high pressure reaction vessel (20 mL/hours) from the feeding bottle with a feeding time of about 2 hours. The total pressure of the CO/H$_2$ was maintained at 50 atm, and the reaction temperature was also maintained at 100±2° C. throughout the reaction. Two hours after the completion of the DCPD feeding, the temperature of the reaction vessel was decreased to the room temperature, and the resulting mixture was phase separated into two layers. The layers were separated and then analyzed by a gas chromatograph (GC). According to the GC data, the cycloalkyl aldehyde had a yield of 99% and a partition coefficient between the upper and lower layer layers of 9.8.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A hydroformylation process, comprising:
   (i) reacting a cyclic olefin with carbon monoxide and hydrogen in the presence of an aldehyde and a rhodium catalyst at a temperature of 40° C. to 160° C. to obtain a hydroformylation product liquid containing cycloalkyl aldehyde;
   (ii) cooling the hydroformylation product liquid to room temperature, and letting the hydroformylation product liquid stand until it divides into a first layer and a second layer, wherein the first layer comprises substantially the rhodium catalyst and a the second layer comprises substantially the aldehyde and the cycloalkyl aldehyde; and
   (iii) separating the first layer from the second layer.

2. The hydroformylation process as claimed in claim 1, wherein the rhodium catalyst is dissolved in a solvent comprising alkane or cycloalkane.

3. The hydroformylation process as claimed in claim 1, wherein the cyclic olefin has single or multi carbon-carbon double bonds.

4. The hydroformylation process as claimed in claim 1, wherein the step of separating the first layer from the second layer is performed at a pressure from atmospheric pressure to 10 MPa.

5. The hydroformylation process as claimed in claim 1, wherein the carbon monoxide and hydrogen have a pressure of 0.5 MPa to 15 MPa.

6. The hydroformylation process as claimed in claim 1, wherein the aldehyde is $C_{1-12}$ aldehyde.

7. The hydroformylation process as claimed in claim 1, further comprising distilling the second layer to separate the aldehyde and the cycloalkyl aldehyde.

8. The hydroformylation process as claimed in claim 1, wherein the aldehyde and the cycloalkyl aldehyde have same chemical formula.

9. The hydroformylation process as claimed in claim 1, wherein the cyclic olefin comprises dicyclopentadiene, tricyclopentadiene, dicyclohexadiene, or cyclohexene.

* * * * *